United States Patent [19]
Hoffmann

[11] 3,932,520
[45] Jan. 13, 1976

[54] 2-METHYL-2-HEPTEN-6-ON-1-AL ACETALS

[75] Inventor: Werner Hoffmann, Ludwigshafen, Germany

[73] Assignee: BASF Aktiengesellschaft, Ludwigshafen am Rhein, Germany

[22] Filed: June 3, 1974

[21] Appl. No.: 476,065

Related U.S. Application Data

[62] Division of Ser. No. 228,266, Feb. 22, 1972, Pat. No. 3,840,559.

[30] Foreign Application Priority Data

Feb. 24, 1971  Germany............................ 2108649

[52] U.S. Cl. .............................................. 260/594
[51] Int. Cl.² ....................................... C07C 49/20
[58] Field of Search ................................... 260/594

[56] References Cited
UNITED STATES PATENTS 2,768,967  10/1956  Bavley et al. ...................... 260/594
3,330,867  7/1967  Saucy................................. 260/594

OTHER PUBLICATIONS

Bhalerao et al., J.A.C.S., Vol. 93, pp. 4835–4840 (1971).

House, Modern Synthethic Reactions, 2nd Edtn. 1972.

Primary Examiner—James O. Thomas, Jr.
Assistant Examiner—James H. Reamer
Attorney, Agent, or Firm—Johnston, Keil, Thompson & Shurtleff

[57] ABSTRACT 2-methyl-2-hepten-6-on-1-al acetals and a method for the production of these compounds. The acetals are obtained by reacting the acetals of 2-methyl-4-halo-2-buten-1-al with an alkali compound of an ester of acetoacetic acid and eliminating, by means of an alkali, the alkoxycarbonyl group from the intermediate obtained. 2-methyl-2-hepten-6-on-1-al is obtained from the acetals by acid hydrolysis. The products are perfumes having a pleasant fruity odor and are intermediates for advantageous synthesis of the natural orange aromatics and orange odorants α-sinensal and β-sinensal.

2 Claims, No Drawings

2-METHYL-2-HEPTEN-6-ON-1-AL ACETALS

This is a division of application Ser. No. 228,266, filed Feb. 22, 1972 now U.S. Pat. No. 3,840,559.

The invention relates to acetals of 2-methyl-2-hepten-6-on-1-al and to a process for the production of these compounds.

The compounds in question have the formula (I):

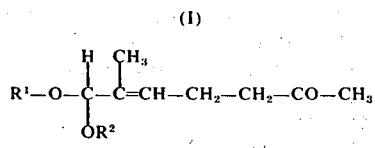

where $R^1$ and $R^2$ is each an aliphatic hydrocarbon radical of one to eight carbon atoms.

I have found that the said compounds can be prepared in a simple way:

a. by reacting anacetal of 2-methyl-4-halo-2-buten-1-al of the formula:

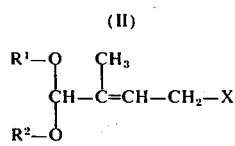

in which X is chlorine, bromine or iodine and $R^1$ and $R^2$ have the meanings given above, at a temperature of from 0° to 100°C with an alkali metal compound of an acetoacetic ester of the formula (III):

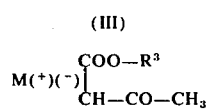

in which $R^3$ is a hydrocarbon radical of one to four carbon atoms and M is an alkali metal;

b. eliminating the $COOR^3$ group from the resultant intermediate of the formula (IV):

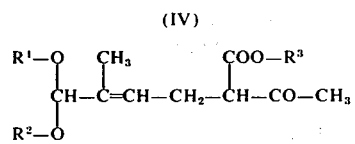

in which $R^1$, $R^2$ and $R^3$ have the meanings given above by alkaline treatment at a temperature of from 20° to 100°C.

This synthesis proceeds smoothly with high yields.

The acetals of 2-methyl-4-halo-2-buten-1-al of the formula (II):

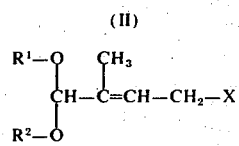

may be those in which $R^1$ and $R^2$ each is an aliphatic hydrocarbon radical such as methyl, ethyl, propyl, isopropyl, n-butyl, isobutyl, n-pentyl, n-hexyl or 2-ethylhexyl-1; $R^1$ and $R^2$ are preferably the same. Methyl and ethyl are particularly suitable as the aliphatic hydrocarbon radicals.

The acetals of the formula (II) can be easily prepared by acetalization of 2-methyl-4-halo-2-buten-1-al which in turn is accessible by treatment of 1,1-dialkoxy-2-methyl-3-buten-2-ol with a thionyl halide or phosgene in the presence of a tertiary amine.

The alkali metal compound of an acetoacetic ester of the formula (III) used is conveniently an alkali metal derivative of an acetoacetic ester of a lower alcohol, i.e., the ester of an alcohol of one to four carbon atoms, particularly of one or two carbon atoms. Although the use of higher esters is possible it does not result in any appreciable advantage.

The alkali metal compounds of esters of acetoacetic acid are prepared by conventional methods, for example, by reaction of an ester of acetoacetic acid with an alkali metal hydroxide or alcoholate at temperatures of from 0° to 50°C.

Preferred compounds of the formula (III) are the sodium and potassium compounds of methyl acetoacetate and ethyl acetoacetate.

The process according to the invention may be carried out in various ways.

Generally a solution or suspension of the alkali metal acetoacetic acid ester is prepared and about 0.9 to 1.2 moles of an acetal of the formula (II) is added per mole of ester at a temperature of from 0° to 100°C, preferably from 10° to 60°C. The reaction requires a reaction period of 0.5 to 15 hours. It may be carried out batchwise or continuously. Examples of solvents or suspending agents are: alcohols such as methanol, ethanol, propanol, butanol, isobutanol and glycol; or hydrocarbons such as benzene, cyclohexane, hexane and decahydronaphthalene. Ethers such as diethyl ether and tetrahydrofuran may however also be used as solvents. Alcohols, particularly methanol or ethanol, are however used as solvents with special advantage.

It is also possible however to introduce the alkali metal compound of an acetoactic ester in powder form slowly and with intense mixing into the acetal of the formula (II). A period of from 30 minutes to 5 hours is necessary for the introduction of the alkali metal compound (III). The total reaction period is then from 30 minutes to 15 hours.

The intermediates of the formula (IV) obtained in the reaction of the alkali compound (III) with the acetal (II) are new compounds. Some of their characteristic data are given in the experimental portion. They do not need to be isolated before they are processed into the desired acetals of 2-methyl-2-hepten-6-on-1-als.

To eliminate the alkoxycarbonyl groups it is advantageous to add to the reaction mixture obtained in the reaction of (II) with (III) an aqueous alkali metal hydroxide solution and to heat the mixture to a temperature of from 20° to 100°C, preferably from 30° to 80°C. Generally from 1 to 4 moles, preferably from 1 to 2 moles, of alkali metal hydroxide in form 5 to 20%, preferably about 10%, solution is used per mole of ester. The necessary reaction period for the elimination of the $—COOR^3$ group is from thirty minutes to ten hours.

When an alcohol has not been used as a solvent in the production of the intermediate (IV) it is advisable to use a lower alcohol, for example methanol, as a solubilizer in the said elimination. The necessary amount approximately corresponds to the amount by weight of water present in the reaction mixture. It is surprising that the COOR³ group can be eliminated by alkaline treatment alone because usually an additional treatment with acids is necessary for such eliminations.

The acetals of 2-methyl-2-hepten-6-on-1-als can be isolated by conventional methods. It is advantageous to isolate them from the reaction mixture by extraction with a conventional extractant, for example with diethyl ether or hexane, drying of the organic phase followed by fractional distillation.

2-methyl-2-hepten-6-on-1-al itself can easily be prepared from the acetals by acid hydrolysis.

The acid hydrolysis is carried out by conventional method. For example, from 0.01 to 1 mole of a mineral acid or organic acid such as sulfuric acid, hydrochloric acid, formic acid, p-toluenesulfonic acid or acetic acid is added to each mole of acetal in the form of a 1 to 20% solution and the mixture is heated for thirty minutes to five hours, preferably from 2 to 3 hours, at a temperature of from 10° to 50°C with intense mixing.

The addition of a lower alcohol as solubilizer is also advisable in this hydrolysis. The ketoaldehyde can be isolated by conventional method, for example, by extraction following mild neutralization of the reaction mixture, for example, with an alkali metal or sodium carbonate followed by distillation of the extractant.

A number of interesting new compounds are accessible for the first time by means of the said process. 2-methyl-2-hepten-6-on-1-al and its acetatals may be used as perfumes with a pleasant fruity odor note. Moreover they are suitable starting materials for the synthesis of the sinensals, desirable component of the natural orange aroma belonging to the terpene series.

The citrus odor of the parent substance 2-methyl-2-hepten-6-on-1-al is overlaid in the case of its acetals by a distinct green note (the odor of grass and hay). It is particularly strong in the case of the acetals derived from methanol and ethanol. It is somewhat less pronounced in the case of the other products. Upon prolonged standing in the air, the odor of the parent substance predominates, because this is liberated by slow hydrolysis. This effect can be utilized reliably in the perfumery industry.

The following Examples will illustrate the invention:

EXAMPLE 1

A. 2-methyl-2-hepten-6-on-1-al dimethylacetal

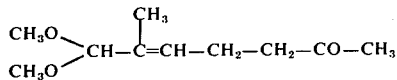

180 g (1 mole) of 30% solution of sodium methylate in methanol is added over 15 minutes at 150° to 20°C to 116 g (1 mole) of methyl acetoacetate. The whole is stirred for another hour at 20° to 30° C and then 156 g (0.95 mole) of 2-methyl-4-chloro-2-buten-1-al dimethylacetal is added to the solution at 20°C over 30 minutes. The reaction mixture obtained is stirred for 15 hours at room temperature, then 400 g of 10% caustic soda solution is added and stirring is continued for another 2 hours at 60°C. The salt-like constituents are separated by filtration and the organic products are isolated by extraction with ether. Before the ethereal solution is distilled it is washed with saturated common salt solution. The ether is then distilled off and the residue is fractionated. The boiling point is 72° to 83°C at 0.9 to 1.5 mm and the refractive index $n_D^{25} = 1.4474$.

B. 2-methyl-2-hepten-6-on-1-al 200 ml of 10% sulfuric acid and 50 ml of methanol are added to 106 g (0.5 mole) of the acetal obtained according to (A) and stirred for 3 hours at 25° to 30°C. Neutralization is then carried out with sodium carbonate and the organic phase is isolated by extraction with ether. After the ether has been distilled off the residue is fractionated. 65 g (93% yield) of 2-methyl-2-hepten-6-on-1-al is obtained. The boiling point is 130° to 140°C at 20 to 23 mm and the refractive index $n_D^{25} = 1.4723$. Note resembling citrus. The odor of the acetals is similar but not so strong.

The following acetals are prepared analogously to Example 1:

2-methyl-2-hepten-6-on-1-al diethylacetal:
Boiling point 74° to 75°C at 0.15 mm; $n_D^{25} = 1.4442$.

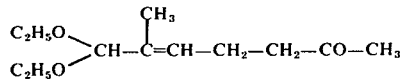

2-methyl-2-hepten-6-on-1-al (2-ethyl-1-hexyl)-bisacetal:
Boiling point 123° to 128°C at 0.01 to 0.05 mm; $n_D^{25} = 1.4615$

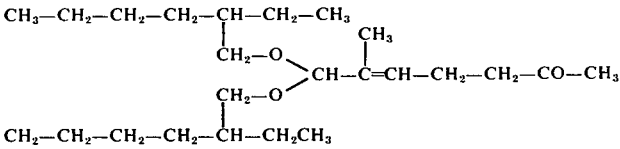

EXAMPLE 2

2-methyl-5-carbomethoxy-2-hepten-6-on-1-al dimethylacetal

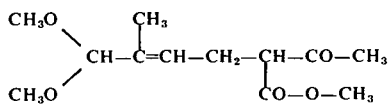

40 g (1 mole) of sodium hydroxide is dissolved in 200 ml of methanol and then 116 g (1 mole) of methyl acetoacetate is added over 30 minutes at 45° to 55°C. Stirring is carried on for another hour at 20° to 55°C and then 198 g (0.95 mole) of 2-methyl-4-bromo-2-buten-1-al dimethylacetal is added at 25° to 37°C over 30 minutes. The reaction mixture is then stirred for 15 hours at room temperature. The methanol is distilled off in vacuo at 20° to 30°C and the residue is extracted with 1 liter of ether. The ethereal solution is washed twice, each time with 100 ml of saturated common salt solution. The ether is then distilled off and the residue is fractionated. The boiling point is 116 to 122°C at 0.8 to 1.0 mm; $n_D^{25} = 1.4514$.

The following intermediates are prepared analogously to Example 2:

2-methyl-5-carboethoxy-2-hepten-6-on-1-al diethylacetal:

boiling point 120° to 126°C at 1 to 1.5 mm; $n_D^{25} = 1.4508$.

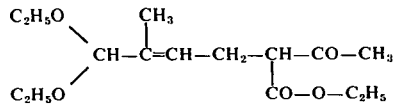

2-methyl-5-carbo-tert.-butoxy-2-hepten-6-on-1-al dimethylacetal:

boiling point 125° to 131°C at 0.5 to 0.8 mm; $n_D^{25} = 1.4516$.

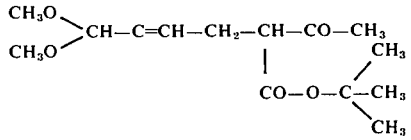

I claim:
1. A compound of the formula (I):

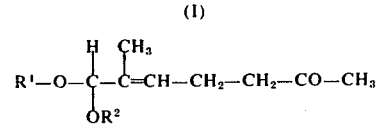

where $R^1$ and $R^2$ each is an alkyl group of one to eight carbon atoms.

2. A compound as set forth in claim 1 wherein $R^1$ and $R^2$ are selected from the group consisting of methyl and ethyl.

* * * * *